United States Patent
Hilliard et al.

(12) 
(10) Patent No.: US 7,147,466 B1
(45) Date of Patent: Dec. 12, 2006

(54) PRESSURE INDICATOR GEL SYSTEM AND METHOD THEREFORE

(75) Inventors: J. Keith Hilliard, Lakeland, FL (US); Dann A. Schwartz, Kenner, LA (US)

(73) Assignee: Dentsply International, Inc., York, PA (US)

( * ) Notice: Subject to any disclaimer, the term of this patent is extended or adjusted under 35 U.S.C. 154(b) by 231 days.

(21) Appl. No.: 10/693,122

(22) Filed: Oct. 24, 2003

(51) Int. Cl.
*A61C 9/00* (2006.01)

(52) U.S. Cl. ........................................ 433/71

(58) Field of Classification Search ............... 433/172, 433/215, 216, 6, 24, 70, 68, 214, 229, 71
See application file for complete search history.

(56) References Cited

U.S. PATENT DOCUMENTS

| | | | |
|---|---|---|---|
| 2,993,276 A * | 7/1961 | Jankelson | 433/172 |
| 3,028,338 A | 4/1962 | Parket | |
| 3,469,439 A | 9/1969 | Roberts | |
| 3,707,771 A | 1/1973 | Guerra | |
| 3,959,881 A * | 6/1976 | Kokal, Jr. | 433/70 |
| 3,992,515 A | 11/1976 | Johnson | |
| 4,198,243 A | 4/1980 | Tanaka | |
| 4,512,741 A | 4/1985 | Mushta | |
| 5,395,239 A | 3/1995 | Komatsu et al. | |
| 6,386,864 B1 * | 5/2002 | Kuo | 433/6 |
| 6,506,368 B1 * | 1/2003 | Lages et al. | 424/49 |

FOREIGN PATENT DOCUMENTS

| | | | |
|---|---|---|---|
| DE | 964060 | | 9/1897 |
| GB | 2250922 A | * | 6/1992 |
| WO | WO 95/05573 | | 2/1995 |

* cited by examiner

*Primary Examiner*—Ralph A. Lewis
*Assistant Examiner*—Meoghan E. MacPherson
(74) *Attorney, Agent, or Firm*—Joseph T. Regard Ltd plc

(57) ABSTRACT

A novel system for discerning pressure points in mouthpieces, namely orthodontic aligners. The system includes the steps of applying a colored gel to a light transmissive or clear mouthpiece-type aligner, mounting the aligner to the upper and/or lower teeth of the patient, and observing through the mouthpiece color variations generated by variations in gel density, wherein pressure points are indicated as lighter colors due to less gel density and spaces are indicated as deeper color, due to higher density of the colored gel. In an alternative embodiment a second gel incorporating rupturable spheres incorporating a second composition is utilized in the present system such that pressure upon the gel releases the second composition, which would be formulated to combine with the first gel and result in a color change, either due to a chemical reaction, or due to a mixing of two colors to produce an identifying color.

30 Claims, 7 Drawing Sheets
(2 of 7 Drawing Sheet(s) Filed in Color)

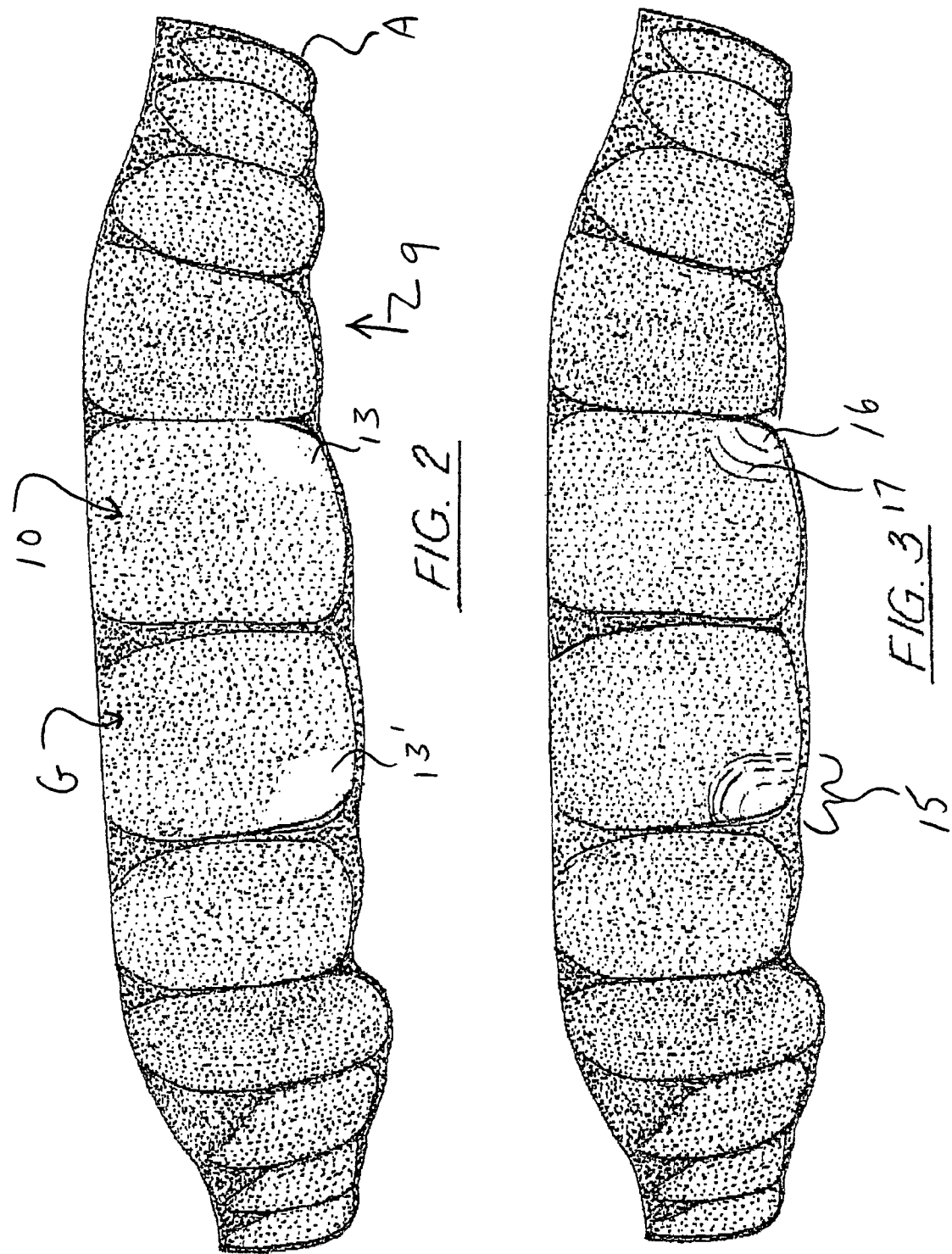

US 7,147,466 B1

PRESSURE INDICATOR GEL SYSTEM AND METHOD THEREFORE

TECHNICAL FIELD OF THE INVENTION

The searched for invention relates to orthodontic dental correction techniques, particularly, a novel system for discerning pressure points in mouthpieces, primarily as used in orthodontic alignment procedures utilizing a gel composition.

The preferred embodiment of the present invention contemplates a system wherein a colored gel is used to provide an indication of spacial depth between a set of teeth and a clear mouthpiece applied thereto.

The preferred embodiment of the present invention contemplates the steps of applying a colored gel to a translucent or clear mouthpiece-type aligner, mounting the aligner to the upper or lower teeth of the patient so that the gel is juxtaposed between the patients teeth and the mouthpiece or aligner, and observing through the mouthpiece color variations generated by variations in gel density, due to pressure points being indicated as lighter colors due to less gel density, with spaces are indicated as deeper color, due to higher density of the colored gel.

The techniques employed in the present invention are particularly useful for indicating the position of the teeth in an aligner, which can be clearly and distinctively preserved in photographic form.

In an alternative embodiment of the present invention, a second gel incorporating gel rupturable spheres incorporating a second composition is utilized in the present system, such that pressure upon the gel releases the second composition, which would be formulated to combine with the first gel and result in a color change, either due to a chemical reaction, or due to a mixing of two colors, to produce an identifying color.

BACKGROUND OF THE INVENTION

Dentists have utilized pressure indicator paste to fit dentures and other dental prosthesis for years. The paste is opaque and generally white in color, and is applied to the denture or appliance where it contacts the patient, which is then applied to the patient, then removed. One then views the paste on the denture or appliance, as well as the patient's teeth to discern impressions in the paste indicating high spots, pressure areas, contact areas, and other disturbances.

Orthodontic aligner mouthpieces have been utilized for years as an alternative to traditional braces to correct misalignment in teeth. These aligner mouthpieces are often fabricated of clear plastic or the like, thermoformed or otherwise manipulated to effect alignment of the wearer's teeth, and applied over the teeth as one would wear a mouth guard. The clear plastic and generally form fitting configuration can make it difficult for a casual observer to notice the aligner.

During an alignment procedure, the aligner is cast about a model of the patient's teeth. The aligner is then manipulated to apply pressure to select portions of the teeth which need alignment. This can be done by observing the teeth which need alignment, approximating the degree, position, and amount of pressure to be applied (which can be accomplished via "bumps" or the like formed on the aligner with special pliers or the like.

However, it can be difficult to judge pressure points, degree, and orientation of the teeth when viewed through the aligner. Further, it can be difficult to judge degree of movement of an aligned tooth or teeth through an aligner during treatment.

U.S. Pat. No. 4,198,243 issued 1980 teaches a liquid glycol colored composition for marking contact points on the occlusal surface of restorative dental or natural teeth.

U.S. Pat. No. 3,707,771 teaches a spray-on composition for detecting dental occlusions by providing a film on the teeth which is ruptured where pressure is applied.

U.S. Pat. No. 4,512,741 teaches "Dental indicating Paste and Method of Use" for fitting dentures or the like.

U.S. Pat. No. 3,992,515 issued 1976 teaches a "Composition for indicating and method of Removing Dental Undercuts and the Like" utilizing a colored composition applied to the teeth. See particularly Column 3, lines 14–36, wherein the composition of the present invention may be applied to a occlusal surface of a restoration and "having the patient bite into centric occlusion and follow with lateral and protrusive movements . . . " so as to "pressure trace the dental indicator composition and indicate where to correct any imbalance of tooth movement excursion"

U.S. Pat. No. 3,028,338 use of fluorescent dye for detecting surface discontinuities.

Regarding the alternative embodiment of the present invention incorporating the utilization of rupturable spheres, U.S. Pat. No. 3,918,160 issued 1975 and teaches the use of pressure sensitive coatings comprising "dispersed cells" applied to teeth, wherein the cells would rupture due to occlusal pressure, producing colored indicia.

U.S. Pat. No. 5,395,239 an "Occlusion Pressure Detecting Sheet" incorporating color containing capsules (14).

U.S. Pat. No. 3,469,439 entitled "Means for Measuring Distributed Forces using Micro capsules" teaches the concept of utilizing rupturable cells to indicate pressure points.

Thus, while the prior art teaches various marking compositions for dental applications, none apparently provide a system utilizing the viscosity and/or light transmissivity properties of a colored gel for suitably discerning orientation, degree, and shape of pressure points, high points, occlusions, spaces, and the like through a transparent or translucent aligner mouthpiece.

GENERAL SUMMARY DISCUSSION OF THE INVENTION

The present invention provides a system for discerning the orientation, degree, and shape of pressure points, high points, occlusions, spaces, and the like through a transparent or translucent mouthpiece-type aligner in a relatively low cost and reliable manner.

In the present invention, a viscous, colored gel material such as, for example, CREST brand gel toothpaste is placed in a mouthpiece-type aligner, and the aligner mounted about the teeth of the patent. The user is then able to view through the mouthpiece the enveloped teeth with the gel dispersed therebetween.

The viscosity and light transmissivity of the gel provides a means to discern space between the teeth and the inner wall of the mouthpiece, both on the labial and lingual sides. Where teeth directly contact the inner wall of the aligner, the color from the gel is lighter or otherwise minimal, and the more space separating the teeth and inner wall of the aligner, the darker the color observed.

It is therefore possible for the user to observe pressure points, and further observe the configuration of the pressure points, degree of pressure, and orientation or occlusion of the teeth forming those pressure points vis a vis the aligner, as these features are highlighted due to their contact with the inner wall of the aligner.

With this information, the user is able to diagnose progress on an aligner in use, including whether a tooth is responding to bias associated with the aligner and, if so, the degree of that response, or if there has been over-correction, under-correction, or mal-correction.

Further, the present technique is easily photographable, providing a means of preserving a record of the position of the patient's teeth during the treatment protocol, for archival and treatment purposes.

It is therefore an object of the present invention to provide a pressure indicator system for use with transparent or translucent mouthpiece-type aligners.

It is another object of the present invention to provide a system for diagnosing progress of response in teeth during correction utilizing mouthpiece-type aligners.

It is another object of the present invention to provide a method of aligning teeth utilizing a mouthpiece-type aligner and a pressure indicator gel.

It is another object of the present invention to provide a pressure indicator paste formulated to provide optimal pressure indication when used in conjunction with a light transmissive, mouthpiece-type aligner.

It is still another object of the present invention to provide a means of indicating the position of a patient's teeth vis-à-vis an aligner during an orthodontic treatment, which is photographable and easily discerned via photographic evidence.

Lastly, it is an object of the present invention to provide a method and system for diagnosing fit of a light transmissive dental appliance utilizing a pressure indicator gel composition.

BRIEF DESCRIPTION OF DRAWINGS

The patent or application file contains at least one drawing executed in color. Copies of this patent or patent application publication with color drawing(s) will be provided by the Office upon request and payment of the necessary fee.

For a further understanding of the nature and objects of the present invention, reference should be had to the following detailed description, taken in conjunction with the accompanying drawings, in which like parts are given like reference numerals, and wherein:

FIG. 2 is a frontal view of the system of FIG. 1 applied to a patent, indicating via lighter areas pressure points on the incisors of the patient.

FIG. 3 is a frontal view of the system of FIG. 2, indicating lines of pressure associated with the pressure points.

DETAILED DISCUSSION OF THE INVENTION

Figure 1:
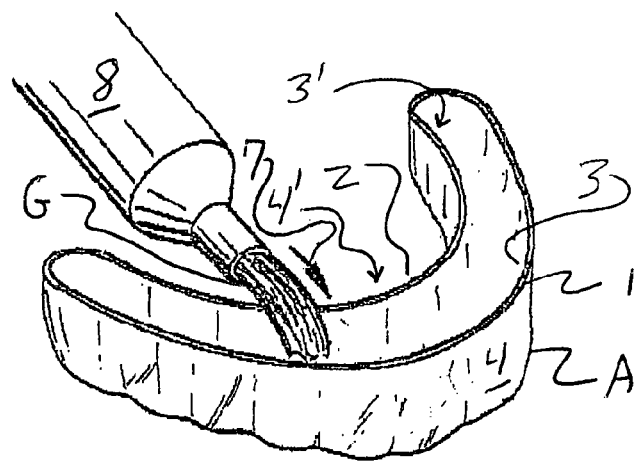
FIG. 1 is an upper, isometric view illustrating a gel composition having light transmissivity properties being applied to the interior of a mouthpiece.
Figure 4:
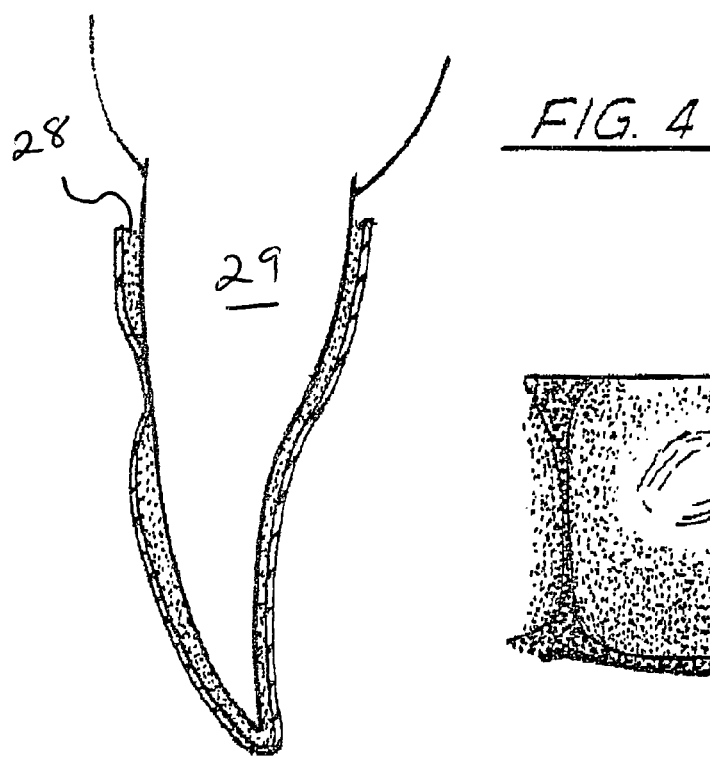
FIG. 4 is a side, cut-away view of the system of the present invention, illustrating a mouthpiece having gel therein applied over a patent's incisor, and a pressure deformation formed in the front face of the mouthpiece to apply pressure to the patent's upper incisor.
Figure 5:
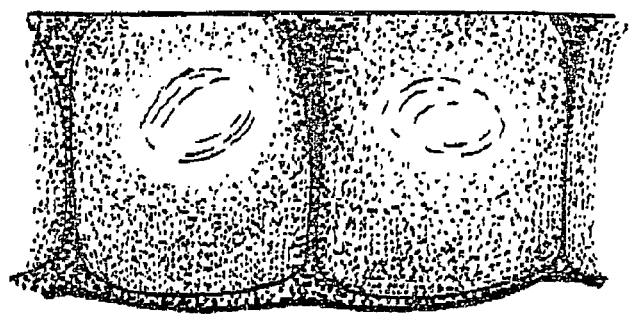
FIG. 5 is a frontal view of FIG. 4, illustrating pressure deformations formed to apply pressure to both upper incisors of the patient.

Continuing with FIGS. 1, 4, and 5 of the drawings, the system of the present invention is intended to be utilized with a clear or translucent mouthpiece aligner a, which may be custom configured to the patent's mouth for an orthodontic straightening of the teeth or other procedure.

As shown, an aligner a typically may include front 1 and rear 2 walls each having interior 3, 3' and exterior sides 4, 4', the walls having a space therebetween forming a cavity 5.

A gel G solution is applied 7 via a tube 8 or other means to the cavity 5 of the aligner in an amount sufficient to fill the space 28 between each tooth and aligner in the area to be observed. In this regard, the gel may be applied to an interior side of the front and/or rear walls at a particular area to be observed, or may be uniformly applied to the bottom of the cavity in an amount sufficient to engage the interior walls of the aligner once it is applied to the teeth of the patient.

Preferably, the gel G of the present system is colored, having a light transmissivity similar to other gel toothpastes such as, for example, CREST brand gel toothpaste or CREST FOR KIDS brand gel toothpaste (the specifications of which are incorporated herein by reference), and a viscosity range of about between, for example, 20,000–80,000 centipoise, and an exemplary viscosity in the preferred embodiment of about 37,000 centipoise, +/−2000 centipoise. The viscosity is important as it allows the gel to remain in place, while easily being displaced with appropriate pressure.

The light transmissivity can also be a factor as a thin layer of gel will have a lesser color density compared to a thicker layer of gel, resulting in an appearance of a lighter color compared to a darker color, respectively.

Ideally, the color of the gel is a darker one such as navy blue, dark green or other dark color, which appears to provide better contrast when viewed through the clear mouthpiece with the teeth of the patient (which typically is of a lighter color) providing the reflective background.

FIG. 2 illustrates an aligner applied 9 to the teeth 10 of a patient, with the gel G juxtaposed between the teeth and the aligner. As shown, pressure points 13, 13' are apparent due to a lighter color 12, with the area between most of the teeth having a relatively uniform color 11 and gaps between the teeth having a darker color 14.

FIG. 3 indicates a color variation 15 of shades within the pressure point indicating the lightest color 16 where the pressure is greatest (thereby displacing most of the gel), to darker shades 17, thereby indicating the degree and orientation of mis-aligned incisors of the patient.

Figure 5A:
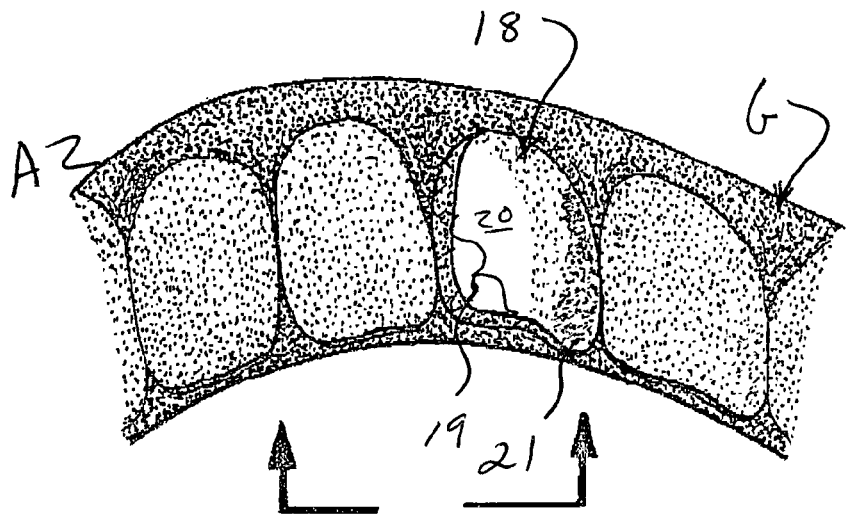
FIG. 5A is a view of the system of FIG. 1 applied to a patent, indicating via lighter areas a pressure point on an incisor of the patient indicative of a tooth which needs alignment.
Figure 5B:
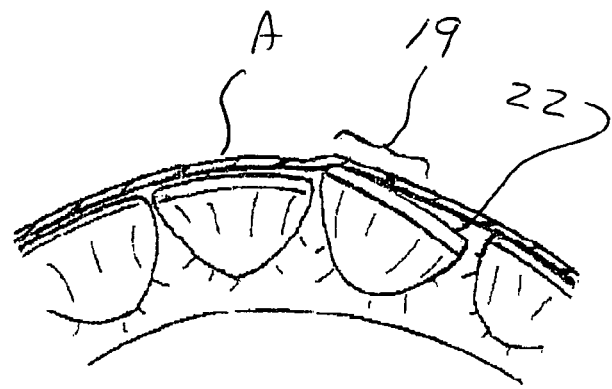
FIG. 5B is a bottom, partially cut-away view of the system of FIG. 5A illustrating the positioning of the pressure point and associated incisor with the front wall of the mouthpiece.
Figure 5C:
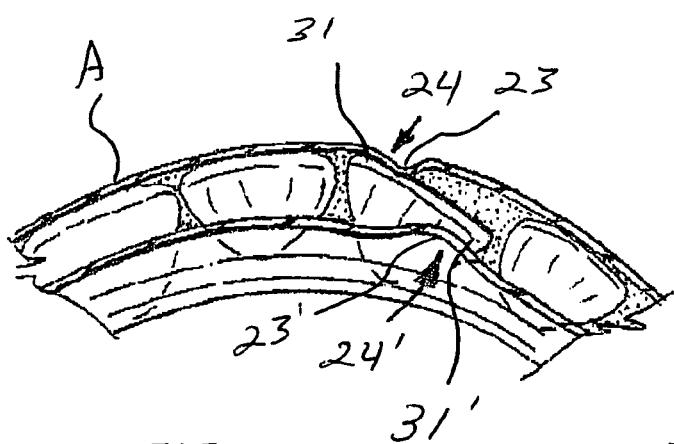
FIG. 5C is a bottom, partially cut-away view of the system of FIG. 5A, indicating pressure deformations formed in the front and rear walls of the mouthpiece to align the tooth and eliminate the pressure point.
Figure 5D:
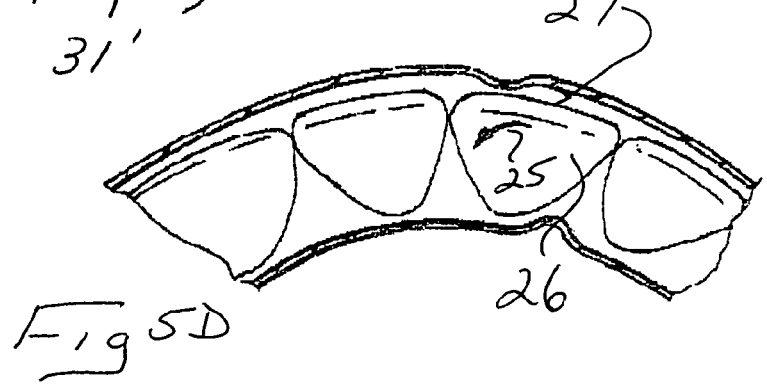
FIG. 5D is a bottom, partially cut-away view of the system of FIG. 5A, indicating alignment of the tooth due to pressure deformations formed in the mouthpiece, and elimination of the pressure point due to the misaligned tooth.

Continuing with FIGS. 5A and 5B, the aligner A, having had gel G dispensed therein, is applied to the teeth of the wearer, revealing a generally uniform color for most of the teeth, yet also revealing an mis-aligned incisor tooth 18 via pressure point 19 visually indicated as a light color area 20, indicating forward protrusion on one frontal side edge of the tooth, as well as a dark colored area 21 indicating an opposing rearward protrusion (in the form of a gap or spacing between said area and the aligner) on the distal side edge of the tooth. Thus, the user may discern that the tooth is in need of an axial correction. Further, the user may utilize this information to approximate the extent of correction required, as well as monitoring progress of said correction.

Utilizing this information, the user may remove the aligner A, and utilize pliers or other tool to form 24, 24' pressure deformations 23, 23' in the aligner a to selectively apply pressure to the opposing sides 31, 31' and edges of the tooth, so as to urge the tooth in axial correction 25, until there is provided a straightened tooth 26 having desired, generally uniform spacing 27 in relation to the aligner.

Further, during this procedure, the user may monitor the degree of axial rotation or other correction utilizing the pressure deformations via the application of gel to the aligner being utilized and applying the mouthpiece with gel to the user. The user may then observe color differentials of the gel through the aligner, thereby indicating differences in spacing of the teeth from the mouthpiece, indicating pressure points and gaps, and allowing the user to estimate the degree of same and overall progress and/or further required corrections.

It is anticipated that, during application of the pressure deformations to the indicated pressure points on the mis-aligned tooth, the indicated light colored area on the aligner will decrease in size and area as the tooth corrects in response to the pressure deformations application of pressure, until such point as the mis-aligned tooth becomes aligned, at which point there should be nominal color differential in the area of the tooth when compared to the other, aligned teeth.

Exemplary specifications for the gel utilized in this procedure are as follows: Viscosity (centipoise) 37000 +/−2000 cP at a shear rate of 30 sec-1, although it is anticipated that the present system could work with a gel having a range of between about 20,000–80,000 centipoise.

Figure 8A:
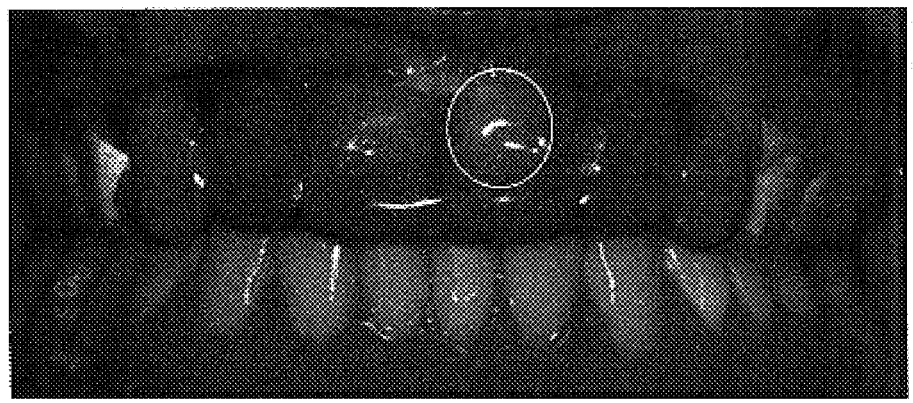
FIG. 8A is a frontal, photographic view of a clear aligner having colored gel applied therein, which is applied to the upper teeth of a patient, and observed to indicate where the patient's teeth contacts the front wall of the aligner, indicated in lighter color.
Figure 8B:
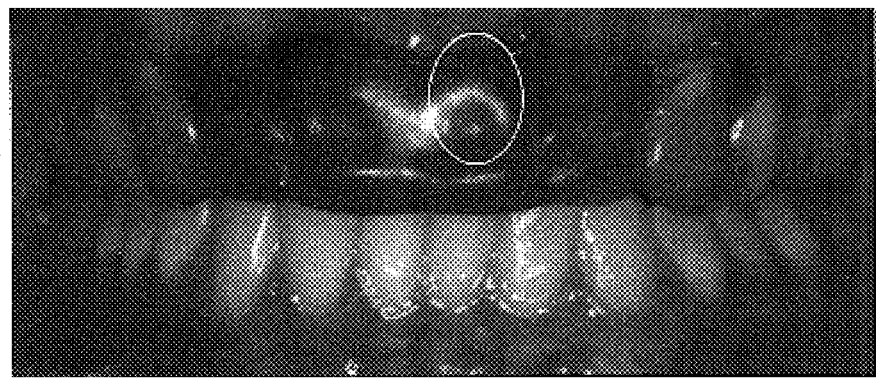
FIG. 8B is a frontal, photographic view of the invention of FIG. 8A, four weeks thereafter, indicating movement and straightening of certain teeth.

Referring to FIG. 8A, a patient has applied thereto a clear aligner A having gel G applied therein, which, when observed, shows a contact area in the form of a clearly discernable lightened area designating contact of the upper right, right central incisor with the interior of the aligner. N FIG. 8B illustrates the same view four weeks later, wherein there is no longer discernable a lightened contact area in the region of the upper right, right central incisor, thereby indicating that said area no longer contacts the aligner as before, and has thereby responded to treatment.

Figure 8C:
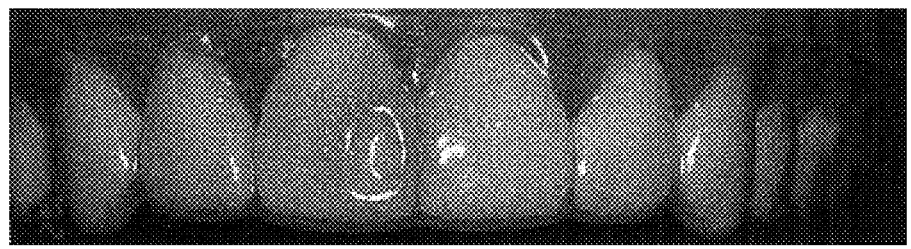
FIG. 8C is a frontal, photographic view of the utilization of the gel of the present invention to indicate spacing between the teeth and the aligner.

FIG. 8C illustrates an alternative use of the system of the present invention, wherein, instead of viewing the lightened area of FIG. 8A, the user views the darkened area to discern spacing of the teeth from the aligner.

An exemplary summary of a method of the present invention could comprise the steps of:

a. applying an aligner and viscous gel solution to the teeth of the patient;

c. allowing the teeth of said patient to displace said viscous gel solution between said aligner and said teeth;

d. photographing said viscous gel solution through said aligner, providing a photograph;

e. analyzing said photograph to determine areas in said aligner where said teeth contact said aligner by discerning visually discernable variations of said gel solution through said aligner, providing contact points;

f. forming pressure deformations in said aligner in the vicinity of said contact points to urge that portion of said teeth contacting said aligner away from said aligner.

It is further noted that steps a–f could be repeated during the treatment, and the previous photographs compared to the present ones to monitor progress and discern appropriate manipulation of the aligner to correct the patient dental mis-alignment in the most efficient manner. In addition, the photographs provide a historical archive of the progress made during the treatment vis-à-vis the retainer, a perspective which was not available until the present invention.

Figure 6A:
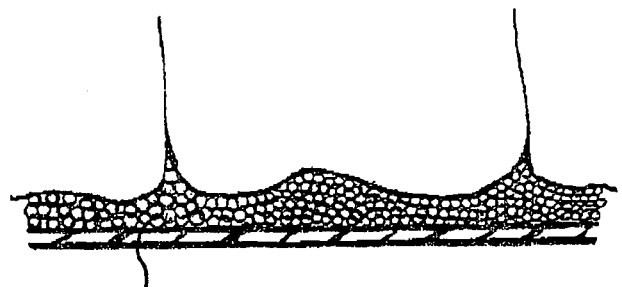
FIG. 6A is a top, cut-away view of a first alternative embodiment of the present invention, illustrating a set of teeth having a mouthpiece having microspheres situated therebetween.
Figure 6C:
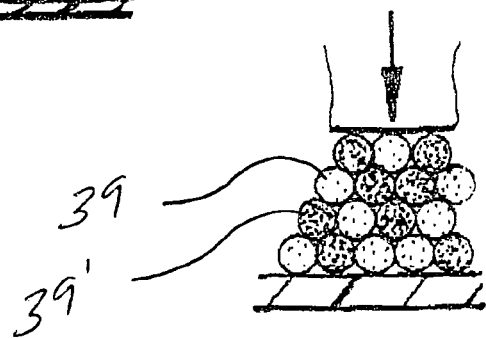
FIG. 6C is a top, cut-away, close-up view of the invention of FIG. 6C, illustrating the microspheres prior to pressure being applied thereto.
Figure 6B:
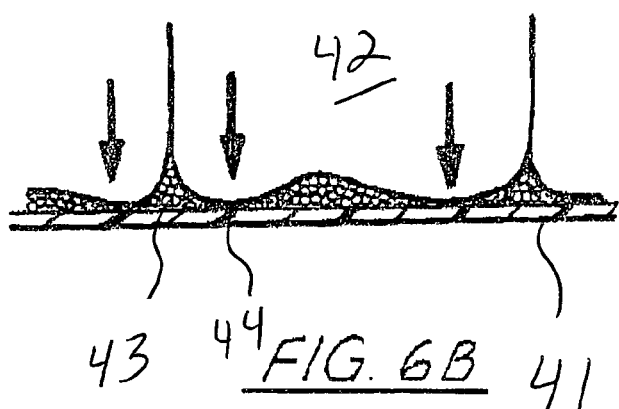
FIG. 6B is a top, cut-away view of the invention of FIG. 6A, illustrating the displacement of the microspheres.
Figure 6D:
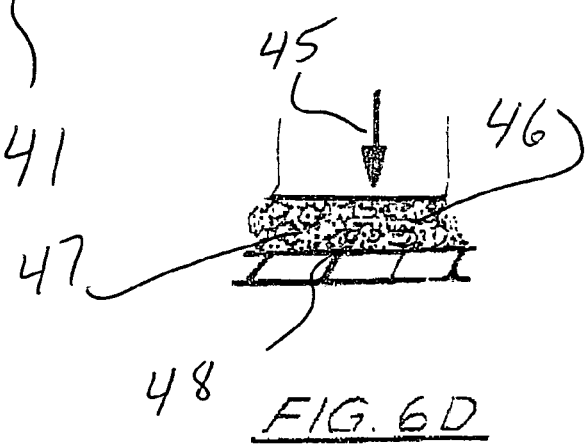
FIG. 6D is a top, cut-away, close-up view of the invention of FIG. 6D, illustrating pressure applied to the microspheres, resulting in rupturing and blending of the contents therein, resulting in color change.
Figure 7A:
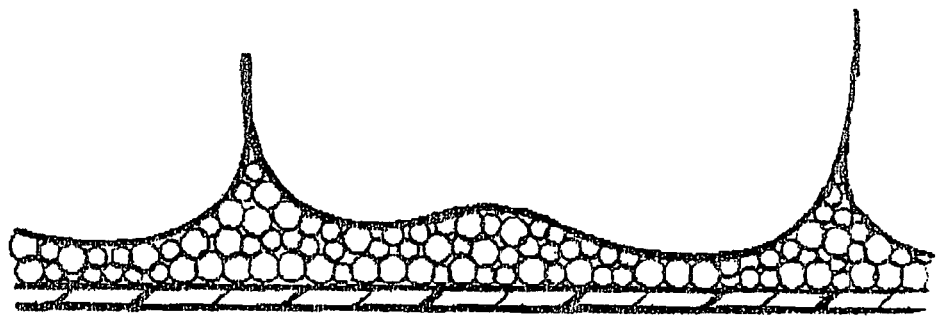
FIG. 7A is a top, cut-away, close-up view of a second alternative embodiment of the present invention, illustrating microspheres having first and second sizes and first and second colors, respectively, situated between a mouthpiece an teeth of a patient.
Figure 7B:
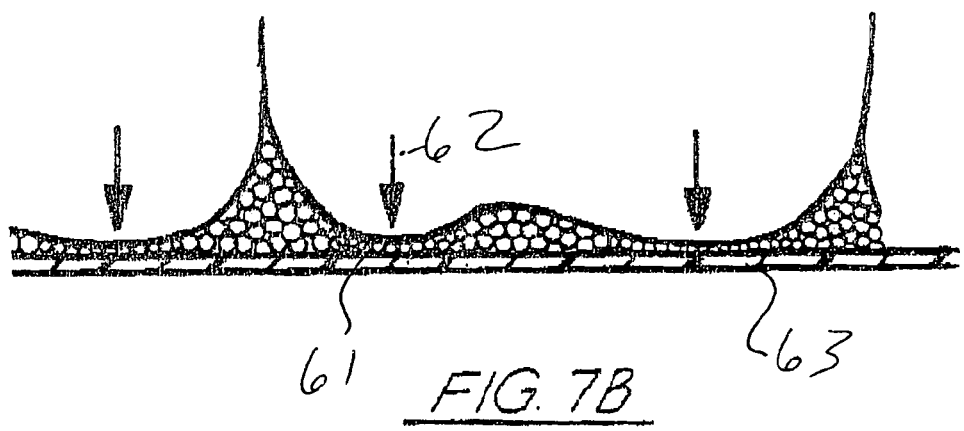
FIG. 7B is a top, cut-away view of the second alternative of FIG. 7A, illustrating pressure applied to the mouthpiece to displace the larger spheres, with the smaller microspheres remaining.
Figure 7C:
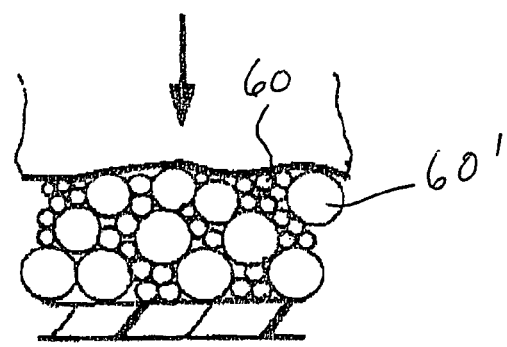
FIG. 7C is a top, cut-away, close-up view of FIG. 7C, illustrating the microspheres of first and second sizes intermingled.
Figure 7D:
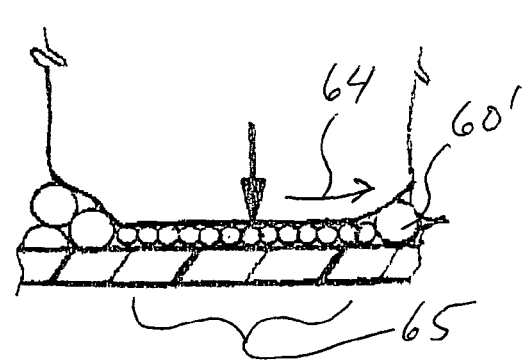
FIG. 7D is a top, cut-away, close-up view of FIG. 7B, illustrating the microspheres of first and second sizes displaced such that the larger microspheres are displaced to voids between the teeth, with the smaller microspheres remaining.

FIGS. 6A and 6C illustrate a first alternative embodiment of the present invention wherein a micropshere composition in a viscous gel carrier 38 is provided, with at least some of the microspheres 39 containing a color change ingredient with reacts with a compound in another 39' of the microspheres, or the gel carrier 38 to provide localized color change where the sphere ruptures upon the application of pressure thereupon. Other indicating means besides color change may also be provided, including chemoluminescent aligner material marking, or other means.

Continuing with FIGS. 6A–6D, in use, the microsphere/gel composition is dispensed between the first and second walls of the mouthpiece-type aligner 41, which aligner with the composition is then applied to the teeth 42 of the patient, wherein mis-aligned teeth forms gaps 43 and pressure points 44 depending upon the distance of the tooth from the aligner, which pressure points apply pressure 45 to and rupture 46 the spheres situated therebetween, so as to provide a chemical composition which blends 47 and which results in a change of color 48, glow or other indication, which may be observed through the aligner, or which may be formulated to mark the aligner itself as a marking device.

Exemplary specification on microsphere/gel composition: Gel: dental gel composition having about 37000 centipoise viscosity +/−2000 centipoise, although operable range is anticipated at being about between 20000–80000 centipoise.

Sphere size, composition, and construction: about 0.5–1 mm, gelatin, edible polymer, or the like, having rupturable, hollow composition having non-toxic color or color change composition therein.

FIGS. 7A–7D illustrate a second alternative embodiment to the present invention, wherein microspheres of first smaller 60 and second, larger 60' sizes are provided, each size having a disparate color, preferably in a viscous suspension, which composition is placed in the aligner 63, and applied to the teeth 62, forming pressure points 61 which urge 64 the larger 60' microspheres away from the pressure areas, resulting in color change 65 due to the lack of larger microspheres in the pressure point areas.

Exemplary sizes of the smaller and larger microspheres are as follows: about 0.25 mm− for smaller spheres 1.25 mm+ larger spheres, although the size could vary depending upon the patient and application.

Exemplary material: food grade silicone, gelatin, edible polymer, or the like.

Exemplary viscosity range of suspension: about 20,000–80,000 centipoise, exemplary viscosity of about 37,000 +/−2000 centipoise.

ELEMENTS OF THE INVENTION

A Aligner
G Gel
1 front wall
2 rear wall
3 interior
4 exterior
5 cavity
6 gel
7 applied
8 tube
9 applied
10 teeth
11 uniform color
12 lighter color
13 pressure points
14 darker color
15 color variation
16 lightest
17 darker shades
18 misaligned tooth
19 pressure point
20 light color area
21 darker area
22 gap
23,' pressure deformations
24,' formed
25 axial rotation
26 straightened tooth
27 uniform spacing
28 space
29 tooth
30 pressure
31 selective pressure
38 Microsphere composition in a viscous gel carrier rupturable microspheres containing first and second compounds or a compound which reacts with gel carrier
41 mouthpiece
42 teeth
43 gaps
44 pressure points
45 pressure
46 rupture
47 blended chemical composition
48 color change, glow or other indication
49 gel
60 microspheres of at least two sizes, each size having a disparite color
61 pressure
62 teeth
63 mouthpiece
64 urges
65 larger microspheres into gaps, smaller microspheres remain resulting in color indication of pressure spot.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. The method of determining the orientation of teeth in a patient,
   comprising the steps of:
   a) applying a mouthpiece and colored gel to the tooth of a patient so as to envelope said tooth, said mouthpiece further applied such that said gel is juxtaposed between said mouthpiece and said tooth;
   b) observing said colored gel through said mouthpiece;
   c) determining the location of contact areas of said tooth to said mouthpiece by noting variations in color as denoted by said colored gel.

2. The method of claim 1, wherein said mouthpiece is an aligner.

3. The method of claim 2, wherein in step "c" said variations in color comprises a lighter color.

4. The method of claim 3, wherein after step "c)" there is further provided the additional step "d)" of determining the location of gaps between said tooth and said mouthpiece by noting darker colored areas as denoted by said colored gel.

5. The method of determining the orientation of teeth in a patient in an aligner, comprising the steps of:
   a. providing a viscous solution;
   b. applying said viscous solution to said aligner;
   c. applying said viscous solution and aligner to said patent;
   d. allowing the teeth of said patent to displace said viscous solution in said aligner;
   e. observing said viscous solution through said aligner;
   f. determining areas on said aligner where said teeth contact said aligner by discerning variations in color through said aligner.

6. The method of correcting mis-alignment in teeth in a patient, comprising the steps of:
   a. applying an aligner and viscous solution to the teeth of the patient;
   b. allowing the teeth of said patient to displace said viscous solution between said aligner and said teeth;
   c. observing said viscous solution through said aligner;

d. determining areas in said aligner where said teeth contact said aligner by discerning visually discernable color variations through said aligner, providing contact points;

e. forming pressure deformations in said aligner in the vicinity of said contact points to urge that portion of said teeth contacting said aligner away from said aligner.

7. The method of claim 6, wherein in step "e" there is provided the step of said patient wearing said aligner for a period of time, and there is provided after step "e." the additional step "f." of repeating steps a–e until there is no longer observed visually discernable color variations through said aligner.

8. The method of claim 7, wherein in step "e" said visually discernable color variations comprises a color tint variation.

9. The method of claim 6, wherein in step "a" said viscous solution has a viscosity range of between 20,000–80,000 centipoise.

10. A method for observing orientation of teeth, comprising:
   a. providing a mouthpiece having first and second walls and an open area therebetween, said mouthpiece formed of light permeable material;
   b. providing a colored gel composition having light transmissivity properties;
   c. applying said mouthpiece to said teeth with said gel composition situated therebetween so that said gel composition fills the voids between said teeth and said mouthpiece;
   d. observing color variations in said gel composition to discern variations of distance between said mouthpiece and said teeth such that uniform spaces between said teeth and said mouthpiece are indicated as a uniform color, pressure points are indicated as a lighter color to said uniform color, and gaps are indicated as a darker color to said uniform color.

11. The method of claim 10, wherein in step "b" said gel composition comprises toothpaste.

12. The method of claim 11, wherein in step "b" said gel composition has a viscosity range of about 20,000–80,000 centipoise.

13. The method of claim 12, wherein in step "b" said gel composition is of a dark color tint.

14. The method of determining the orientation of teeth through an aligner, comprising the steps of:
   a. providing a layer of colored gel composition having light transmissive properties between said aligner and said teeth;
   b. utilizing said light transmissive properties of said colored gel composition to indicate via color variations, variations in the space between said teeth and said aligner;
   c. observing said color variations through said aligner to discern variations in the space between said teeth and said aligner.

15. The method of determining the orientation of teeth through an aligner, comprising the steps of:
   a. applying a colored gel to a light transmissive or clear mouthpiece-type aligner;
   b. mounting said aligner with said gel to the teeth;
   c. allowing said teeth to displace said gel within said aligner;
   d. observing through said aligner color variations generated by variations in the depth of said gel, wherein pressure points are indicated as lighter colors due to less gel depth and spaces are indicated as deeper color, due to greater depth of the colored gel.

16. A method for observing orientation of teeth, comprising:
   a. providing a mouthpiece having first and second walls and an open area therebetween, said aligner formed of light permeable material;
   b. providing a gel having a plurality of rupturable microspheres containing color indicia;
   c. applying said mouthpiece to said teeth with said gel situated therebetween so that said gel fills the voids between said teeth and said mouthpiece,
   d. allowing said microspheres to rupture upon the application of pressure at contact points where the teeth contact said aligner so as to dispense said color indicia means at said contact point, providing dispensed color indicia.

17. The method of claim 16, wherein in step "d.", said dispensed color indicia is visually observed through said aligner.

18. The method of claim 16, wherein in step "d.", said color indicia is utilized to mark said aligner in the vicinity of said contact point.

19. A method for observing orientation of teeth, comprising:
   a. providing a mouthpiece having first and second walls and an open area therebetween, said mouthpiece formed of light permeable material;
   b. providing a gel composition having a plurality of colored microspheres;
   c. applying said mouthpiece to said teeth with said gel composition situated therebetween such that said microspheres are displaced from contact areas where said teeth contact said aligner, so as to provide visually discernable indication of said contact areas through said aligner.

20. The method of determining the orientation of teeth in a patient in an aligner, comprising the steps of:
   a. providing a viscous solution;
   b. applying said viscous solution to said aligner;
   c. applying said viscous solution and aligner to said patent;
   d. allowing the teeth of said patent to displace said viscous solution in said aligner;
   e. photographing said viscous solution through said aligner, providing a photograph;
   f. analyzing said photograph to determine areas on said aligner where said teeth contact said aligner by discerning variations in color as denoted by said viscous solution through said aligner.

21. The method of correcting mis-alignment in teeth in a patient, comprising the steps of:
   a. applying an aligner and viscous solution to the teeth of the patient;
   b. allowing the teeth of said patient to displace said viscous solution between said aligner and said teeth;
   c. photographing said viscous solution through said aligner, providing a photograph;
   d. analyzing said photograph to determine areas in said aligner where said teeth contact said aligner by discerning visually discernable color variations of said solution through said aligner, providing contact points;
   e. forming pressure deformations in said aligner in the vicinity of said contact points to urge that portion of said teeth contacting said aligner away from said aligner.

22. The method of claim 21, wherein there is provided the additional step "f" of repeating steps a–e, until said misalignment has been corrected.

23. The method of claim 21, wherein said solution comprises a gel.

24. The method of claim 21, wherein said solution has a viscosity range of between 20,000–80,000 centipoise.

25. The method of claim 15, wherein said gel has a viscosity range of between 20,000–80,000 centipoise.

26. The method of claim 15, wherein said gel comprises toothpaste.

27. The method of claim 5, wherein said viscous solution comprises a gel.

28. The method of claim 27, wherein said viscous solution is colored.

29. The method of claim 28, wherein said viscous solution has a viscosity range of between 20,000–80,000 centipoise.

30. The method of claim 1, wherein said gel has a viscosity range of between 20,000–80,000 centipoise.

* * * * *